(12) United States Patent
Fleming et al.

(10) Patent No.: US 6,948,369 B2
(45) Date of Patent: Sep. 27, 2005

(54) METHODS FOR ULTRASONIC INSPECTION OF SPOT AND SEAM RESISTANCE WELDS IN METALLIC SHEETS AND A SPOT WELD EXAMINATION PROBE SYSTEM (SWEPS)

(75) Inventors: Marvin F. Fleming, Los Altos, CA (US); Jack P. Clark, San Jose, CA (US)

(73) Assignee: Applied Metrics, Inc., Fremont, CA (US)

( * ) Notice: Subject to any disclaimer, the term of this patent is extended or adjusted under 35 U.S.C. 154(b) by 0 days.

(21) Appl. No.: 11/034,674

(22) Filed: Jan. 12, 2005

(65) Prior Publication Data

US 2005/0132809 A1    Jun. 23, 2005

Related U.S. Application Data

(63) Continuation of application No. 10/361,714, filed on Feb. 6, 2003, now abandoned.

(60) Provisional application No. 60/354,688, filed on Feb. 6, 2002.

(51) Int. Cl.⁷ ............................................. G01N 29/10
(52) U.S. Cl. ........................... 73/588; 73/620; 228/104
(58) Field of Search .......................... 73/588, 597, 598, 73/620, 644; 228/104

(56) References Cited

U.S. PATENT DOCUMENTS

| 3,832,889 A | 9/1974 | Bauer ........................ 73/71.5 |
| 4,208,917 A | 6/1980 | Aoyama et al. .............. 73/644 |
| 4,265,119 A | 5/1981 | Dubetz et al. ................ 73/588 |
| 4,454,764 A | 6/1984 | Sorenson ..................... 73/642 |
| 4,734,555 A * | 3/1988 | Ferguson .................... 219/109 |
| 5,228,343 A | 7/1993 | Schoenen et al. ............. 73/644 |
| 5,469,744 A * | 11/1995 | Patton et al. ................. 73/644 |
| 5,473,943 A | 12/1995 | Schoenen et al. ............. 73/644 |
| 5,537,875 A | 7/1996 | Viehmann et al. ............ 73/588 |
| 5,804,730 A | 9/1998 | Pfannenstiel et al. ......... 73/622 |
| 5,814,731 A | 9/1998 | Alexander et al. ............ 73/644 |
| 5,952,577 A | 9/1999 | Passi ........................... 73/618 |
| 6,072,144 A | 6/2000 | Perryman ................... 219/109 |
| 6,298,727 B1 | 10/2001 | Fleming et al. .............. 73/644 |
| 6,532,820 B1 | 3/2003 | Fleming et al. .............. 73/627 |

FOREIGN PATENT DOCUMENTS

JP         361223648 A    10/1986

* cited by examiner

*Primary Examiner*—John E. Chapman
(74) *Attorney, Agent, or Firm*—Allston L. Jones

(57) ABSTRACT

An external focused ultrasonic beam, non-destructive, open-air, inspection method of sheet metal spot and seam weldments using a probe in combination with motion measurement of the probe over the weldments during inspection without immersion of the material. Reflected ultrasonic waves are received and signals produced and processed or displayed as A-scan, B-scan and C-scan images that are easily recognized. An A-Scan is based on the time-of-flight difference between the outer surface, the weldment and inner and opposite surfaces of the component. B-scan and C-scan indicate the degree of weld fusion and provide data relative to fused thickness and defects sheet metal or welds. A special purpose scanner that enables ultrasonic examination welds. Scanner is pencil like ultrasonic probe with bearing face and position sensing device disposed adjacent a weld position. Scanner collects data for method to determine various characteristics of welded items.

16 Claims, 11 Drawing Sheets

Electrode Specifications and Dimensions

| | Electrode Type(mm) | 1 | 2 | 3 | 4 | 5 | 6 | Tol. |
|---|---|---|---|---|---|---|---|---|
| A | Dressed Face Diameter | 4.5 | 5.0 | 6.0 | 7.0 | 8.0 | 9.0 | ±0.1 |
| B | Face Diameter | 4.5 | 4.9 | 5.9 | 6.9 | 7.9 | 8.9 | ±0.1 |
| C | Body Diameter | 15.9 | 15.9 | 15.9 | 19.0 | 19.0 | 22.0 | ±0.1 |
| D | Length | 29.0 | 29.0 | 29.0 | 32.0 | 32.0 | 32.0 | ±0.2 |
| E | Shank Length | 12.7 | 12.7 | 12.7 | 15.9 | 15.9 | 15.9 | ±0.2 |
| F | Face Thickness | 9.7 | 9.7 | 9.7 | 9.7 | 9.7 | 9.7 | ±0.5 |
| G | Hole Diameter | 8.1 | 8.1 | 8.1 | 9.7 | 9.7 | 12.7 | ±0.3 |
| | Taper Loc. per Ford Spec. | 9.9 | 9.9 | 9.9 | 13.4 | 13.4 | 13.4 | ±0.1 |
| | per RWMA Spec. | 9.9 | 9.9 | 9.9 | 12.7 | 12.7 | 12.7 | ±0.1 |
| H | Taper Dia. per Ford Spec. | 10.54 | 10.54 | 10.54 | 14.33 | 14.33 | 17.81 | ±0.01 |
| | per RWMA Spec. | 10.54 | 10.54 | 10.54 | 12.725 | 12.725 | 15.57 | ±0.01 |
| T | Taper Angle* | 1.43° | 1.43° | 1.43° | 1.43° | 1.43° | 1.43° | ±0.05° |
| Angle | Bevel Angle | 45° | 45° | 45° | 45° | 45° | 45° | ±1° |

Figure 11

METHODS FOR ULTRASONIC INSPECTION OF SPOT AND SEAM RESISTANCE WELDS IN METALLIC SHEETS AND A SPOT WELD EXAMINATION PROBE SYSTEM (SWEPS)

This application claims priority from U.S. Provisional Application Ser. No. 60/354,688 filed Feb. 6, 2002, and is a continuation of utility patent application having Ser. No. 10/361,714 and filed on Feb. 6, 2003, now abandoned.

BACKGROUND OF THE INVENTION

1. Field of the Invention

This invention relates to a specialized scanner and method of inspecting the integrity of spot and seam welds and more particularly it relates to an ultrasonic, nondestructive method of inspecting spot and seam welds.

2. Description of the Prior Art

Heretofore, the inspection of spot and seam welds has been performed using visual, radiographic and ultrasonic methods; as described in the Nondestructive Testing Handbook (Metals Handbook, 9th Edition, Volume 17, "Nondestructive Evaluation and Quality Control", ASM International, Metals Park, Ohio, September, 1989, pg. 335) and the Metals Handbook (Nondestructive Testing Handbook, 2nd Edition, Volume 7. "Ultrasonic Testing", American Society for Nondestructive Testing, Columbus, Ohio, 1991, pgs. 10–12 and pgs. 557–566). The visual and radiographic methods reveal little or nothing concerning the fusion of these welds. The prior art ultrasonic method referred to in the literature as a pulse-echo method however is generally referred to as a ring down technique throughout the industry (Nondestructive Inspection of Spot Welds, Overview of Symposium held at Center for Nondestructive Evaluation Nov. 6, 1997). It makes use of the reflected amplitude and the envelope formed in time by many multiple reflections. Basically an envelope of these reflections are used to indicate if the weld is fused or not. Destructive sampling techniques of welds have also been in use. This has been done by either separating the sheets with a chisel or with a tensile pull technique. Another destructive technique in common use cuts through the weldment, polishes and enhances the weldment so that the dimensions of the fused part of the weld can be measured optically. In this prior art, (Recommended Practices for Test Methods for Evaluating the Resistance Spot Welding Behavior of Automotive Sheet Steel Materials, SAE publication ANSI/AWS/SAE/ D8.9-97; Specification for Resistance Welding of Carbon and Low-Alloy Steels, American Welding Society, AWS C1.4M/ C1, 4:1999), the part is destroyed and the dimensions of the weld are used to infer the weld quality.

Although there are many ultrasonic transducers and scanners in the prior art none has adapted to the features needed to measure the unique parameters and topology encountered in spot welds. The prior art has used immersion scanners for making B-scan and C-scan images that are convenient for making the measurements required. This process requires the part be placed in a tank of water having sufficient volume to immerse the spot weld being inspected, orienting the part to the transducer and scanner axis and drying the part afterwards. The immersion tank must fit the largest part and, as a result is usually too large to be made portable. The water in the tank requires conditioning and adds to the size of the system. A skilled operator is required to use such equipment to make proper images.

It would be advantageous to have a technique and system that includes the capability to accurately measure dimensions of fusion in the weldment and to determine the presence of weld defects. Using the dimensions of the fused sections as a quality indicator would make the ultrasonic process highly reliable and accurate and save on industrial injury which sometimes occurs during the expensive destructive quality tests of welds. Additionally, a compact, lightweight scanner that is better adapted to the scanning needs of spot weld inspection in a factory environment is needed, one that can make all the measurements, in the manufacturing environment, and require lessor skills and training. The present invention provides such a technique and system, as well as a compact, lightweight scanner design.

SUMMARY OF THE INVENTION

Spot and seam weldments in sheet metal components are non-destructively inspected by a method in which a focused ultrasonic beam is directed into the weldment from the outside surface together with a means for measuring the motion of the ultrasonic beam over the weldment without the welded material being immersed in water or some other liquid. Reflected ultrasonic waves are received and signals indicative thereof are produced and processed or displayed as image forms that are easily recognized by an operator. This data is displayed as an A-Scan where a predetermined time window is established on the display, based on the time-of-flight difference between the outer surface, the weld interface or interfaces and the inner or opposite surface of the component. Certain ultrasonic signals are indicative of the degree of complete fusion in the weld zone and provide data relative to the total fused thickness and to defects either in the sheet metal or in the weld.

A manual or mechanized scanner is used to move the ultrasonic transducer in a predetermined scanning motion on the surface of the part at a constant height stand-off distance. This ultrasonic transducer both generates the transmitted waves and receives the reflected waves from the weldment. Coupling of the ultrasonic transducer to the component is achieved via a continuous liquid couplant column (usually water filled). Encoder readings are received from the scanner, which provides dimensional data, relating the position of the ultrasonic transducer on the surface of the part. By combining the ultrasonic and the encoder data, B and C-Scan images (cross sectional and plan views) of the component are generated and displayed. These images are easily used to determine the quality of the weldment in question. These displays are then used to measure the diameter of spot welds, the distance between spot welds, the length and widths of seam welds plus the size, shape and location of defects, such as porosity or lack of fusion, within the weldments, plus laminar type defects, either in the base material or the weld zones.

A "pencil like" probe having an interchangeable tip is used to perform inspections of spot weldments in sheet metal components. This probe can be hand manipulated for scanning purposes, or can be attached to some mechanical scanners. The hand manipulation permits the examination of spot welds that are in locations with minimal or tight clearances, in locations on complex surfaces and orientations, and in locations where access is limited and complex. The probe is elongated to allow the user some flexibility in gripping the probe.

In order to make a useful inspection of the spot weld, some bearing means is required for moving the probe against and across the spot weld area of sufficiently uniform rate and to position an ultrasonic transducer at a sufficiently uniform space above the spot weld area. The hub tip bearing surface material is selected to facilitate easy scanning. The tip of the probe uses an interchangeable "hub" having a diameter large enough to traverse the surface marks made by the welding electrodes during the welding process.

The encoder is attached to a clamp to a top plate by a rod connecting it to the probe housing. The clamp serves as a position reference to the top plate using a magnetic clamp, a vacuum clamp or, if used on a reasonably level surface, clamping can be accomplished by a sufficiently weighty block.

These features when combined in this fashion, result in a feasible and portable scanner that is capable of making a broad range of nondestructive spot weld measurements without the need for an immersion tank.

BRIEF DESCRIPTION OF THE DRAWINGS

FIG. 11 provides sample dimensions for a weld electrode as shown in FIG. 10.

DETAILED DESCRIPTION OF THE INVENTION

The spot and seam type welds used to attach two or more sheets, or plates, of metal together are addressed, as shown, in FIGS. 1, 2, 3, 4, 6 and 7 where the measurement of fused weldment dimensions is one of the objectives of the present invention. Since ultrasonic waves penetrate a fused weld zone, the method of the present invention is capable of non-destructively, in open-air, determining the length of a continuous fused section(s) which easily relate to weld strength without immersing the material being tested in water or another liquid. Additionally, ultrasound is sensitive to common weld defects which will be seen below.

Figure 1:
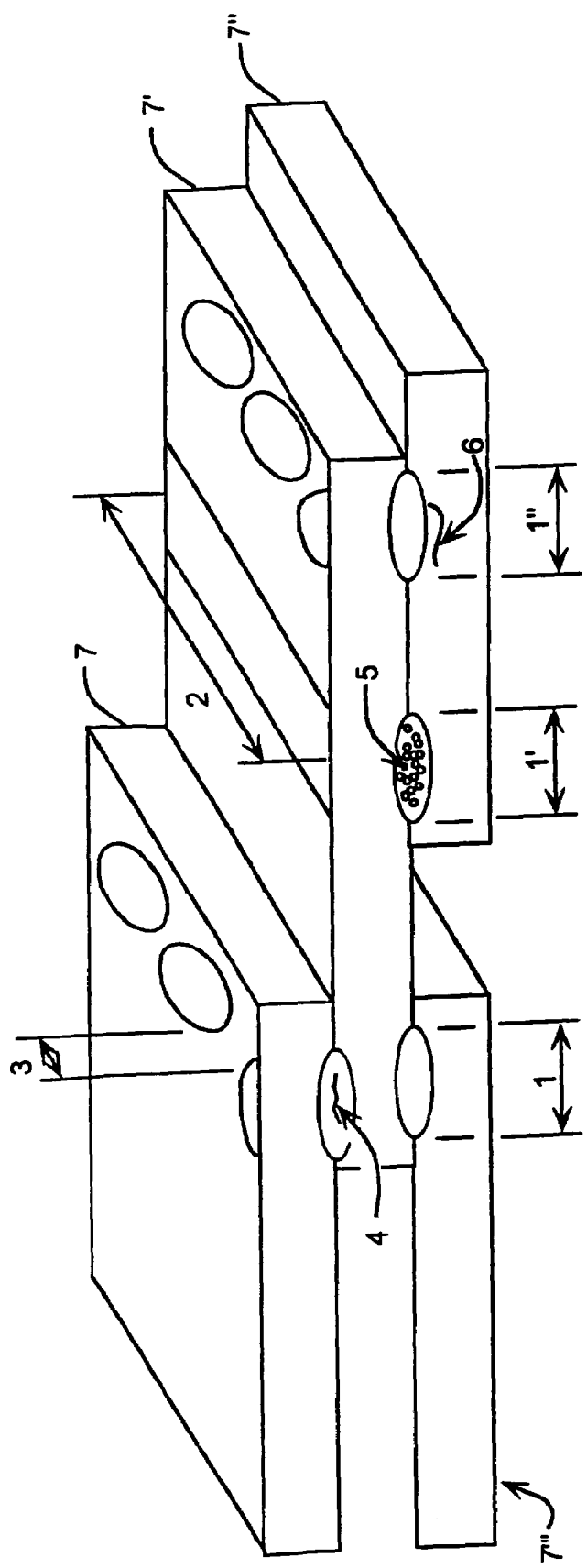
FIG. 1 is a perspective view of four metal plates that overlap various degrees of each other to illustrate typical spot and seam welds.

The present invention uses a focused ultrasonic beam with a means for encoding transducer movement to measure the length and penetration of a fused weldment. The present invention uses an ultrasonic transducer selected to provide a signal with a frequency that will be transmitted by properly fused weldments and blocked, or refelcted by weldment defects. The focused ultrasonic beam is also used to measure critical lengths of fusion in both spot and seam welds as shown in FIG. 1. The dimensions labeled 1, 1', 1" represent the length of the spot welds depicted, 2 represents the length of the fusion zones of the seam weld depicted and 3 represents the distance between fusion zones, the welds being made in the welded plates (or sheets) 7, 7', 7", 7"' as depicted in FIG. 1. Defect dimensions and location are also measured by the present invention; such as those illustrated as weld lack of fusion 4, porosity 5 or laminar defects 6 as illustrated in FIG. 1.

Spot and seam weld(s) of the types illustrated in FIG. 1 are normally used to fuse two or more sections of sheet metal together. As such they can be considered as a lap type joint. They are produced by placing electrodes in contact with opposing surfaces of the sheets to be fused and directly in line with each other. A predetermined amount of pressure is applied to assure good contact of the electrodes with the metallic surfaces and good contact between the surfaces to be joined. An electrical current is then passed from one electrode to the other flowing through the metal sheets generating heat in the metal. The proper combination of heat and applied pressure results in a portion of the surfaces of the two sheets being welded, or fused, together. Normally the position of such welds can only be seen visually due to a slight surface depression caused by the pressure of the electrodes and possibly by some discoloration due to the heat. Naturally the size of the actual fusion zone is critical to the integrity of the component as is the detection of defects which could jeopardize the integrity of the weld itself. Such defects include lack of fusion within the weld zone (4), porosity (5) and laminar type defects (6), either in the weld, or in the base material of the sheets adjacent to the fused areas. In the case of a series of spot welds the distance between the fused zones of the welds can have a direct effect on the overall strength of the welded component.

All of these quality related features can be detected, measured and evaluated using the present invention. FIG. 1 is a diagram showing the different types of resistant weld configurations and include illustrations of defects such as the lack of fusion in a weld and plate laminations adjacent to a weld edge. The dimensions of interest in determining weld strength can be measured; such as the length of the fusion zones of spot welds, the distance between spot welds plus the length and width of seam welds. To accomplish this, a beam of ultrasound (typically 5–25 MHz) is directed into the metal sheets just above the area of fusion.

Since the velocity of sound in metals has been predetermined and is known, the time of flight of the ultrasonic beam in the material is directly related to the distance the beam travels to reach and return from a reflector. In the case of two or more metal sheets that have been fused together, that distance will be the total combined thicknesses of the two sheets; if there is no fusion zone or if the fusion is incomplete the distance traveled will be much less. All of this data is processed by a data acquisition system (see FIG. 8) into commonly used displays (Nondestructive Testing Handbook, Volume II. Edited by the Society for Nondestructive Testing, Ronald Press, N.Y. 1963, pgs 43–34 through 43–36). It can be displayed as amplitude (intensity) vs. time on an oscilloscope type display both in real time or at some convenient later time using data storage techniques.

Figure 2:
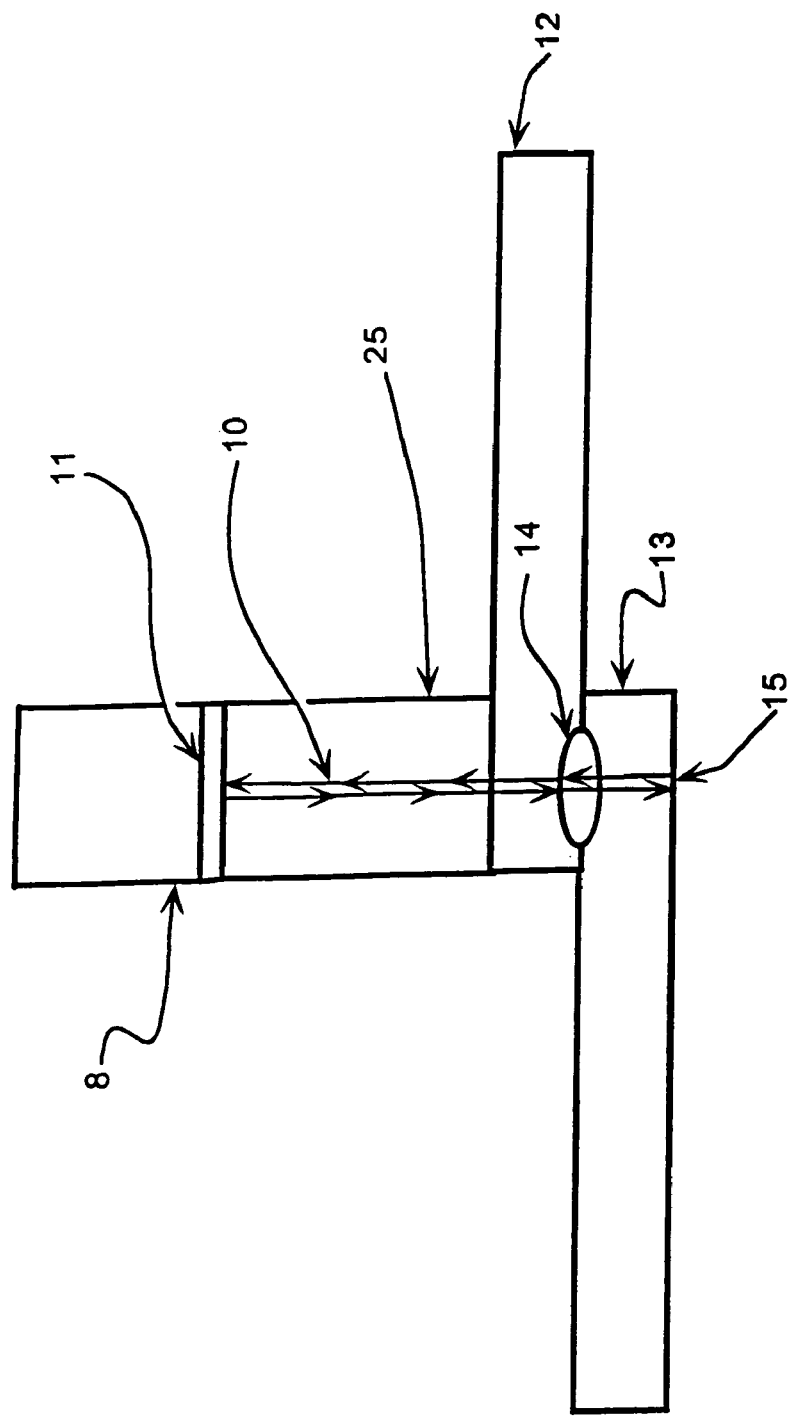
FIG. 2 is a simplified side plan view of the ultrasonic transducer and liquid column of the present invention showing ultrasonic propagation to and from the metal plates and the weld.

FIG. 2 is a simplified diagram of an ultrasonic probe 8 including an ultrasonic transducer 11 and a liquid column 25. The ultrasonic transducer 11 produces an ultrasonic beam 10, that passes through liquid column 25 (typically water filled), directed to the top of upper plate 12. Beam 10 passes through the top of the entry plate 12 to a weld 14. If fusion has occurred (i.e., weld 14 is a good weld) beam 10 will pass through weld 14 and through the near side of bottom plate 13. In that situation ultrasonic beam 10 is be reflected back to transducer 11 from bottom surface 15 (the far surface of plate 13) (where two or more plates are joined together typically referred to as lap welded). If fusion has not occurred, or a lack of fusion exists, or some other discontinuity is present (i.e., a poor or incomplete weld), beam 10 will not pass through fusion zone 14 and instead is reflected back to transducer 11 from the far side of plate 12 instead of surface 15 as discussed above for a good weld. As probe 8 is moved relative to the surface of plate 12 at a constant height stand-off distance to a location above a point where there is no fusion zone between plates 12 and 13, or if weld 14 is poor, ultrasonic beam 10 will be reflected back from the far-side of plate 12, instead of from surface 15.

Figure 3:
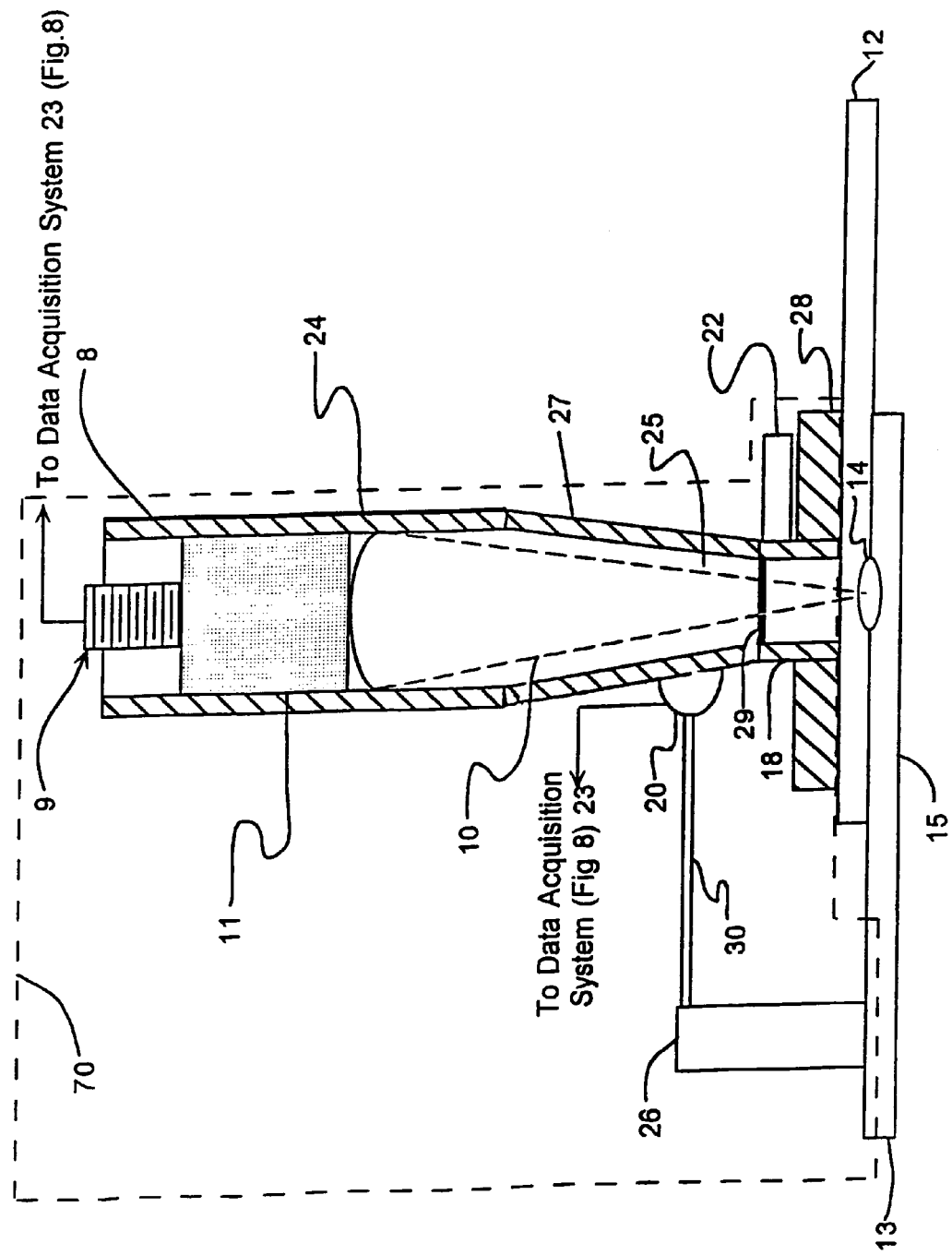
FIG. 3 is similar to FIG. 2 with details of a transducer scanner added.

FIG. 3 adds more details to that which is shown in FIG. 2. Here scanner 70 includes ultrasonic probe 8, position encoder 20, replaceable nose piece 28, rod 30 and traction clamp 26. Within probe housing 24 of probe 8 is ultrasonic transducer 11 and liquid column 25 (introduced in FIG. 2), and a data connector 9 at the distal end to connect ultrasonic transducer 11 to a data acquisition system 23 (see FIG. 8). The proximate end of probe housing 24 includes a cone section 27 that tapers down to a cylindrical tip 18. At the juncture of cone 27 and tip 18, there is a membrane 29 to retain the liquid within liquid column 25. Tip 18 makes contact with the surface to be scanned with nose piece 28 surrounding the lower portion thereof and having a couplant inlet 22 shown extending laterally into the upper region of tip 18. To allow measurement of different size welds of interest, the diameter of nose piece 28 can be varied by selecting one with a, diameter that complements the weld size. The couplant between the top surface of sheet 12, and tip 18 and nose 28 is typically water that is supplied via couplant inlet 22 from a source not shown.

Position encoder 20 is connected to the exterior of probe housing 24 close to the surface being scanned. Coupled to encoder 20 (shown extending to the left) is rod 30 that is connected to traction clamp 26 that is in contact with the top surface of the workpiece being scanned (top of bottom sheet 13 in this view). Encoder 20 also provides an output signal to data acquisition system 23 (see FIG. 8). Tip 18 of probe 8 is shown in contact with the top surface of sheet 12 of the workpiece, as in FIG. 2, to examine weld 14 between plates 12 and 13 using focused ultrasonic beam 10 delivered through cone section 27. Encoder 20 measures the lateral movement of probe 8 relative to the surface of the workpiece. The output signals from encoder 20 and transducer 11 are routed to an ultrasonic data acquisition system 23 (see FIG. 8).

Transducer 11, for the inspection of welds, normally has a frequency range of 5 to 25 MHz, depending on the material and thickness to be examined (e.g., sheets 12, 13). Additionally, the material of membrane 29 is selected to be thin and essentially transparent to ultrasonic beam 10 at the frequencies of interest. As mentioned above, the proximate section of housing 24 consists of a cone 27 angled so that the focused ultrasonic beam 10 only exits through a small hole in tip 18, where probe 8 contacts plate 12 to perform the desired examination. Cone 27 is shown filled with a couplant (usually water or another liquid) that is sealed therein by membrane 29. If desired, a couplant inlet (not shown) could also be provided to the interior of probe assembly 24 to replenish any couplant which may slowly escape, as desired or as the result of a leak from one of the components. Alternatively, couplant entering tip 18 from couplant inlet 22 could also provide the coupling medium for the focused ultrasonic beam 10 to travel through cone 27 and to wet the workpiece surface to couple ultrasonic beam 10 to plate 12.

The focused ultrasonic beam 10 allows the size of cone 27 to be minimized and to yet provide high spacial resolution to weld 14.

Additionally, traction clamp 26 provides a position reference from the workpiece using either a magnetic clamp, a vacuum clamp or, if used on a reasonably level surface, traction clamp 21 could be a sufficiently weighty block. Alternately, encoder 20 could be mounted to a portion of probe 8 other than that shown in FIG. 3. Normally probe 8 is hand held and scanning is performed manually; however, a motor driven scanning mechanism could also transport probe 8.

Replaceable nose piece 28 sliding on the high point of the plate 12 provides improved accuracy in first plate height measurements (distortion 93 and indentation depth 90 in FIG. 9) as probe 8 is moved along plate 12. Nose piece 28 acts as a bearing and provides a steady reference against plate 12, allowing accurate measurements of the surface, thickness and electrode impression of plate 12.

As a result of the combination of probe 8, encoder 20, clamp 26 and selectable nose piece 28, measurements in addition to those of the quality of an internal weld are practical by using the present invention. Examples of height related dimensions include: the measurement of high points in the weld area, the depth of defects, the welded thickness and the depth of indentation of the surfaces at the point of the weld. Also, the shape, the orientation and/or the diameter of the weld electrode indentation can be measured relative to the surface of the top plate using this probe. The shape of the welding electrode can also be measured. In addition, the thickness of the finished weldment can be measured. Further, any combination of the above parameters can be measured.

If traction clamp 26 is a traction wheel with encoder 20 connected to the center axis thereof, as probe 8 is moved, the traction wheel rolls along the top surface of plate 12 with that rotation converted to distance traveled by encoder 20, which provides position information when the starting point of the scan is known and thus the location of transducer 11 with respect to weld 14 can be determined. Use of a typical position encoder 20 to measure the relative location of the ultrasonic transducer 11 accomplishes the acquisition of the essential ultrasonic data related to weldment dimensions in front of, and behind, the plane depicted in FIG. 3 (top and bottom surfaces of sheets 13 and 12, respectively).

In FIG. 3 transducer 11 is focused so the focal zone includes the working depth of the welds of interest. In some cases, particularly when using larger diameter beamwidths for focused ultrasonic beam 10 on uneven or distorted surfaces, a flexible membrane may be added above the contact surface of probe 8 (see U.S. Pat. No. 6,298,727), so that the bottom of liquid column 25 takes the shape of the distorted surface and good coupling is maintained.

The steadiness gained by sliding nose piece 28 of probe 8 over or across the high point of the weld is also compatible with a commonly used ultrasonic technique known as "surface following" or "automated surface following" and is utilized in the ultrasonic signal processing current practice.

The present invention includes the elements of a system that are used to accurately measure the aforementioned dimensions in the weldment and to determine the presence, the location, the shape and to classify weld defects. Obtaining the ultrasonic measurements of weldment dimensions is non-destructive and provides a highly reliable, timesaving, unique and accurate means of determining the quality of spot welds.

Figure 4:
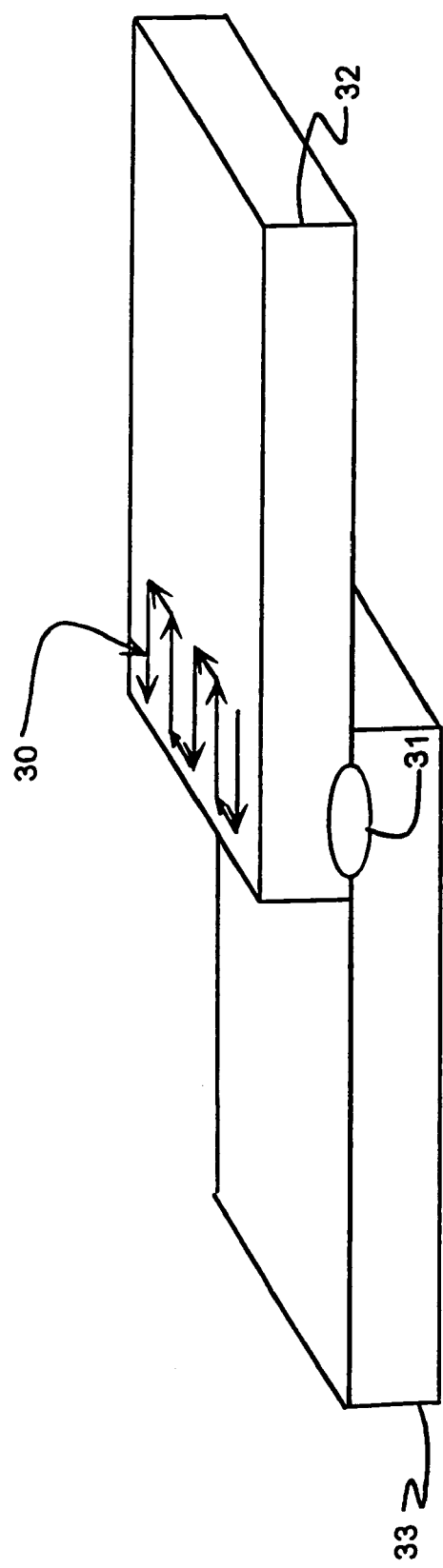
FIG. 4 illustrates a combination x and y axis scan pattern on the surface of a first plate at the location of a seam weld with a second plate.

FIG. 4 is a sketch illustrating two plates 32 and 33 attached one to the other by weldment 31. To obtain a C-scan of weldment 31, a scanning pattern 30 as shown in FIG. 4 is used. The prior art contains several means for evaluating the weld dimensions from the ultrasonic data such as commonly referred to as A-scans, B-scans and C-scans (Metals Handbook, 9th Edition, Volume 17, "Nondestructive Evaluation and Quality Control", ASM International, Metals Park, Ohio, September, 1989, pg. 335; Nondestructive Testing Handbook, 2nd Edition, Volume 7. "Ultrasonic Testing", American Society for Nondestructive Testing, Columbus, Ohio, 1991, pgs. 10–12 and pgs. 557–566). In order to collect a proper B-scan the operator must use the same judgment for positioning the ultrasonic beam as used in positioning the weldment cuts for the destructive evaluations. A raster scan eliminates the need for accurate positioning of the B-scan by employing the C-scan ultrasonic techniques. This is especially useful when evaluating a seam weld as shown in FIG. 4.

Figure 5A:
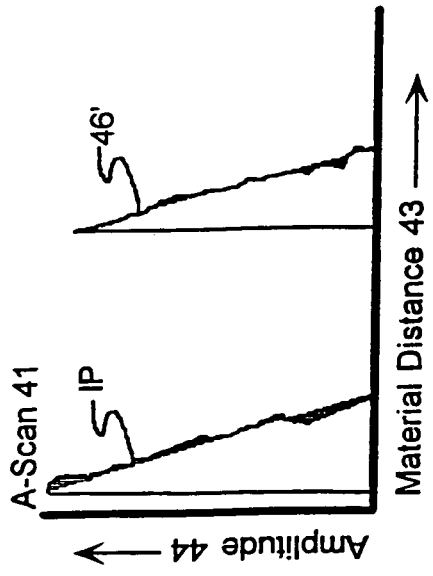
FIGS. 5, 6 and 7 illustrate the use of ultrasonic techniques using A-scans, B-scans and C-scan to evaluate spot and seam weldments.
Figure 5B:
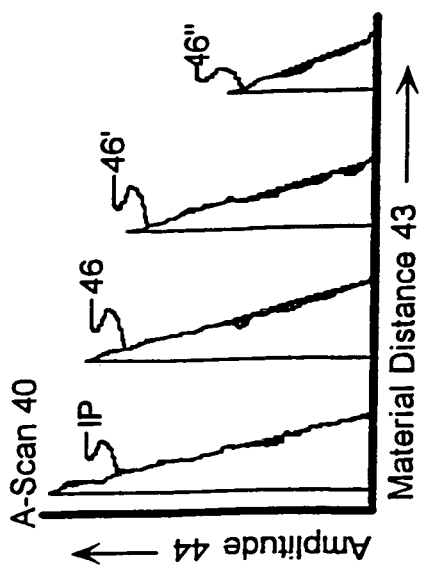
Figure 5C:
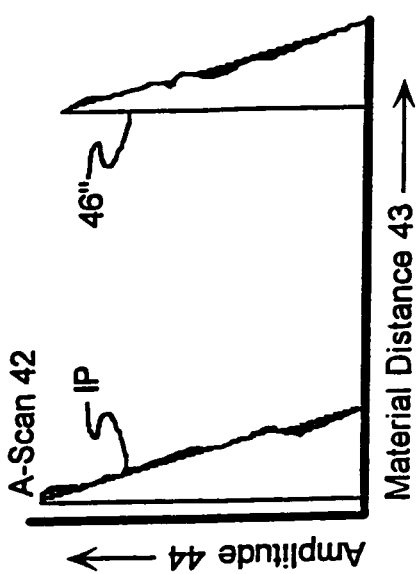

Turning now to FIGS. 5A, 5B and 5C with each illustrating an oscilloscope displays of a typical A-Scan of reflected ultrasonic signals from different reflectors associated with the welds, as shown in FIGS. 1 and 2. In each of FIGS. 5A, 5B and 5C, the horizontal axis of each A-scan is calibrated in time lapse after the initial pulse, IP, or distance 43 into the material and the vertical axis is calibrated in amplitude 44 of the signals. FIG. 5A shows an A-scan 40 of reflections 46, 46' and 46", at intervals of one thickness of a plate 7 in FIG. 1, that correspond to a situation where there is no fusion between two plates, which is the same as the reflections of a single plate, i.e., the reflections for an interval of one thickness of a plate taken on the left side of plate 7 in FIG. 1. Note, the time lapse (or material distance 43) starting with the IP and continuing with 46, 46' and 46" represent the same values in each of FIGS. 5A, 5B and 5C. FIG. 5B shows an A-scan 41 of reflections 46' that correspond to a point where there is full fusion between two plates such as weld 14 between plates 12 and 13 in FIG. 2. A-scan 41 of FIG. 5B also represents reflections that correspond to a point on a stack of three plates where there is full fusion between the top and middle plates and a lack of fusion between the middle and bottom plates, thus the reflections are from the bottom surface of the middle plate 7' which is substantially the same as the reflections from two plates with full fusion between them. FIG. 5C shows an A-scan 42 of reflections 46" that correspond to a point on a stack of three plates where there is full fusion between the top and middle plates 7 and 7' and full fusion between the middle and bottom plates 7' and 7" with the two fusion points being substantially aligned with each other.

Figure 6A:
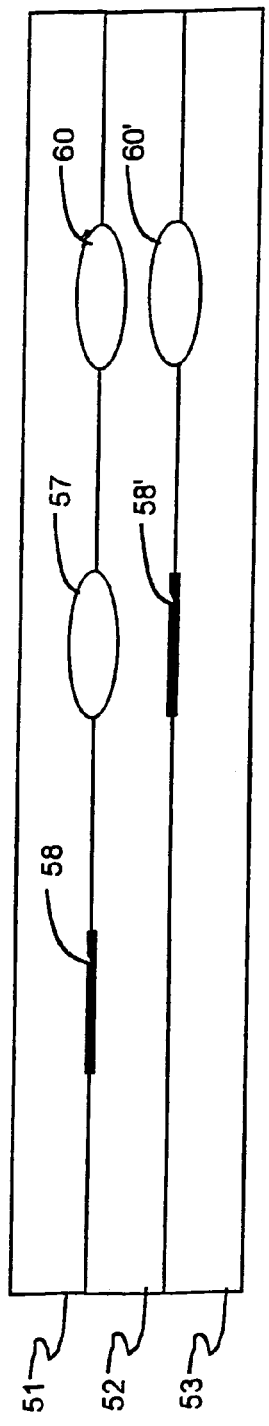

FIG. 6A is a cross-section view that shows a number of different weldments between plates 51, 52 and 53 from top to bottom, one on top of the other. Starting from the left there is a point 58 that lacks fusion between plates 51 and 52 where an attempted weld has failed and there is no weld between plates 52 and 53. Approximately in the center of FIG. 6A, proceeding horizontally left to right there is a point 57 where there is good fusion between plates 51 and 52 and the lack of fusion at point 58' between plates 52 and 53, immediately below point 57. Proceeding further to the right in FIG. 6A, there is a point 60 where there is full fusion between plates 51 and 52 and full fusion at point 60' between plates 52 and 53, immediately below point 60.

Figure 6B:
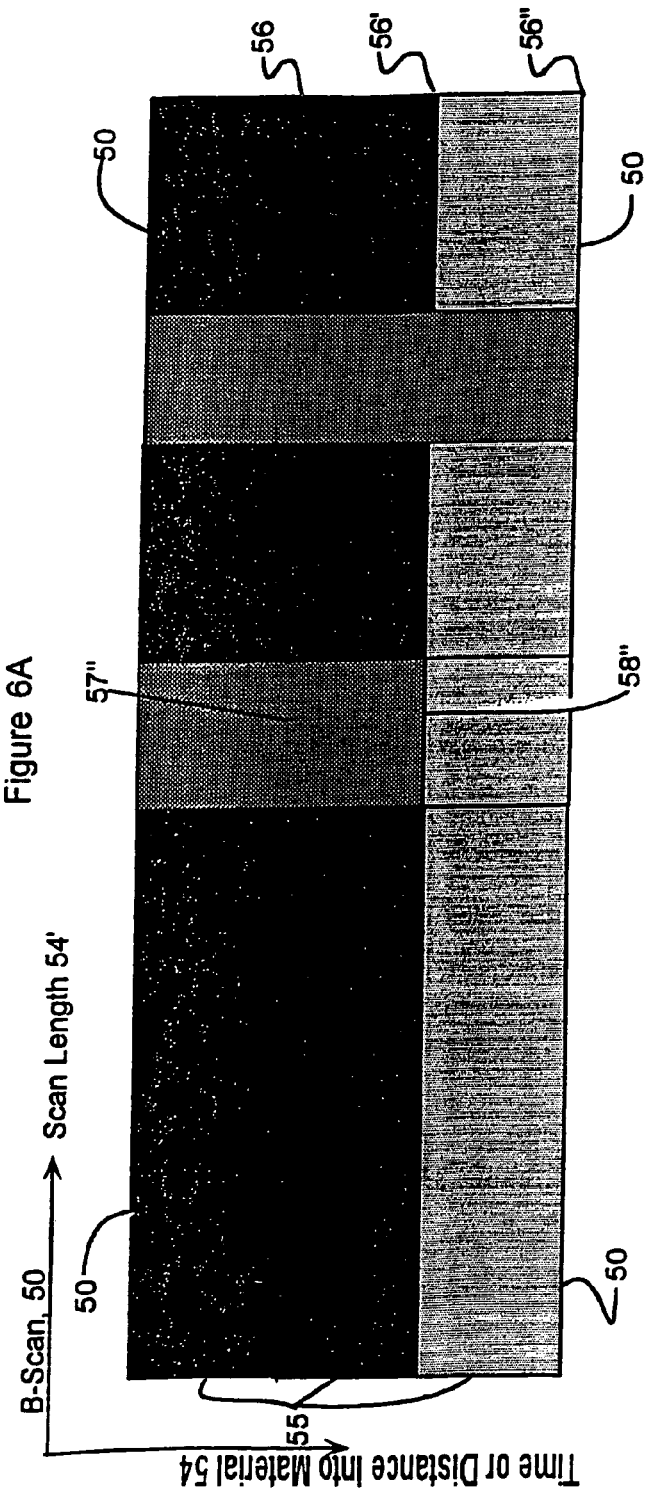

FIG. 6B, in lateral alignment with FIG. 6A, shows a B-scan 50 (see Metals Handbook, 9th Edition, Volume 17, "Nondestructive Evaluation and Quality Control", ASM International, Metals Park, Ohio, September, 1989, pg. 335) cross-sectional image of the three plates and weldments of FIG. 6A. The use of a B-scan is useful for making a recordable image of the quality of the weldment with the B-scan image being a plot created from a combination of the continuous digitization and storage of ultrasonic A-scan data (FIG. 5) and the positional data from encoder 20 (FIG. 3). The B-scan 50 horizontal axis is the length traveled along the surface of the component being inspected by probe assembly 8 containing ultrasonic transducer 11 that produces focused ultrasonic beam 10 (in this case along the top of plate 51 in FIG. 6A). The vertical axis is the time of flight 54 (time of flight 54 is equated to distance below the top surface of the top plate 51) of the ultrasonic signals from the reflectors encountered. The amplitude of the ultrasonic signals vary as the sound propagates through the material and can also be displayed using a color code or a grey scale 55 at any combination of scan length 54' and distance 54 into the material. The location of the transition amplitude peaks 46, 46' and 46" from the A-scans of FIGS. 5A, 5B and 5C correspond to the gray scale transitions 56, 56' and 56" in the B-scans of FIGS. 6A and 6B.

Note that in B-scan 50, other than in alignment with, and below welds 57 and 60 in FIG. 6A there is no variation, i.e., all three gray scale color bands are shown indicating that there is no, or poor, fusion between any of plates 51, 52 and 53 in those regions. In the center of B-scan 50, corresponding to where there is good fusion between plates 51 and 52 at weld 57, and poor fusion at attempted weld 58' between plates 52 and 53 in FIG. 6A, there is an absence of a color transition at interface 56' thus indicating that weld 57 is a good quality weld between plates 51 and 52. The width of the weld image 57" is directly related to the width of the fusion in weld 57 in FIG. 6A. The lack of fusion of attempted weld 58' between plates 52 and 53 results in a transition line in the B-scan image 50 in the area 58" that corresponds to the return 46' in A-scan 41 of FIG. 5B. Full fusion of the plates in welds 60 and 60' in FIG. 6A produces no transition in the B-scan image at levels corresponding to 56 and 56', however the reflection from the bottom of plate 53 produces a transition at level 56" below the weld fusions 60 and 60'. The length 57" of the B-scan made with a focused ultrasonic beam 10 represents a measure of the length of weld 57 along the scan length 54'. This important relationship affords a new and different means for evaluating spot welds. The A-scan 42 of FIG. 5C produced when the ultrasonic transducer is over welds 60 and 60' shows a response 46" corresponding to the transition at 56" in FIG. 6B. The width of the B-scan image in this region corresponds to the width common to welds 60 and 60' and the corresponding full fusion quality of those welds.

Figure 7B:
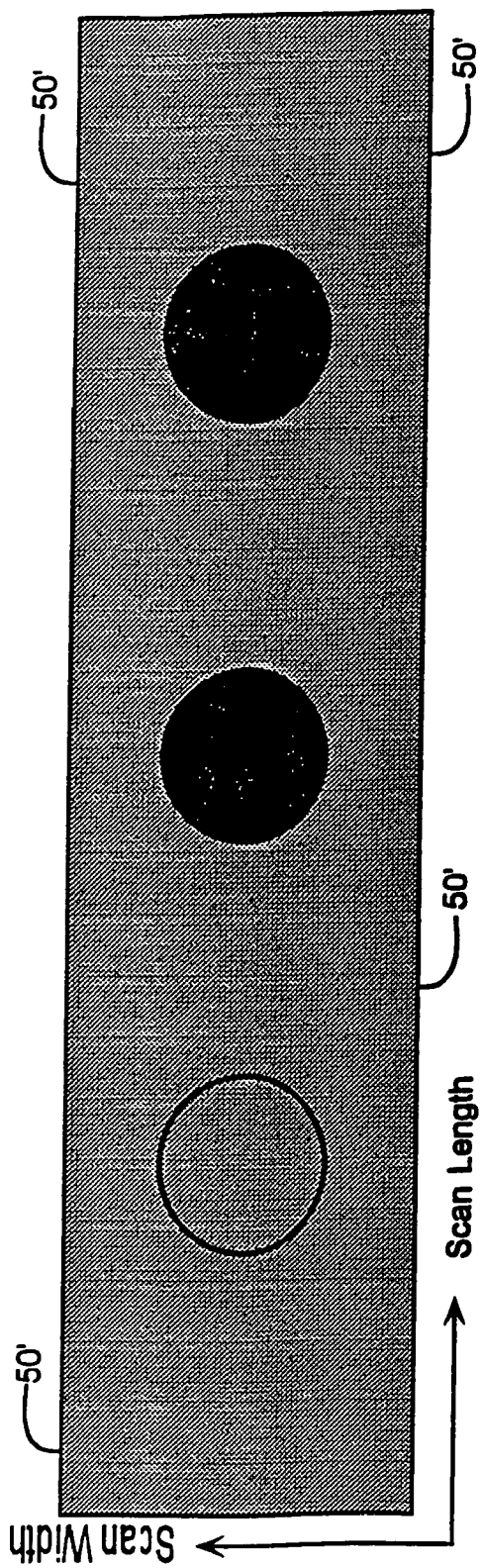
Figure 7A:
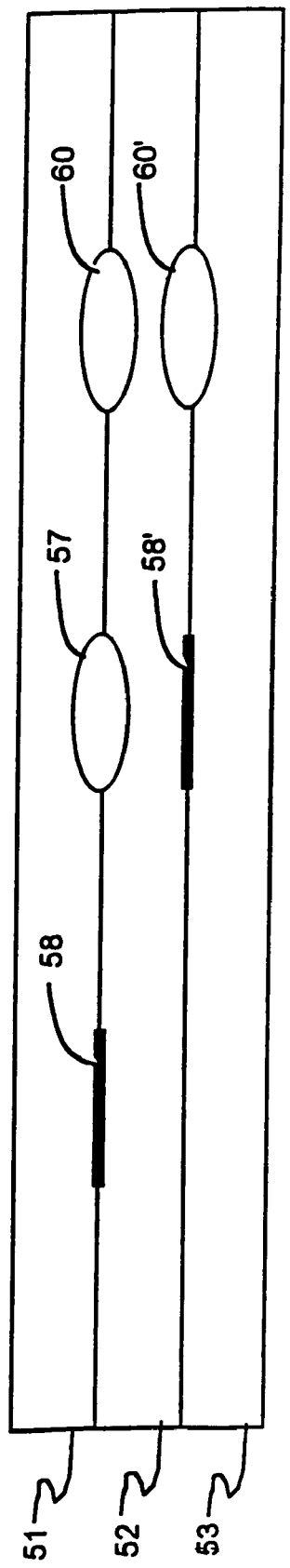

The concepts of the A- and B-scans extend to include the use of C-scans for evaluating the area dimensions for spot welds. FIG. 7A is the same cross-sectional view of the workpiece as in FIG. 6A. FIG. 7B, in lateral alignment with FIG. 7A, illustrates a typical plan view C-scan image 50' of the weldments of FIG. 7A that are being inspected. The vertical and horizontal axes of the C-scan image show the width and the length of the area scanned, respectively, (obtained from encoder 20) and include images showing the quality and the location of the ultrasonic reflectors. With this type of image either the amplitude or the time of flight of the signals from the ultrasonic reflectors can be displayed using a color code or a gray scale. The C-scan is especially useful for determining the quality of seam welds by measuring the width and area, and the continuous length of the fusion area.

In FIG. 7B there is no change in the gray scale of the C-scan in the region corresponding to the lack of fusion at attempted weld 58 in FIG. 7A. In the regions of the C-scan that correspond to the good fusion at weld 57 and full fusion at welds 60 and 60' in FIG. 7A both produce substantially the same gray scale color change and are shown circular assuming that the weldments at points 57, 60 and 60' are each circular and extend into the plane of FIG. 7A.

Figure 8:
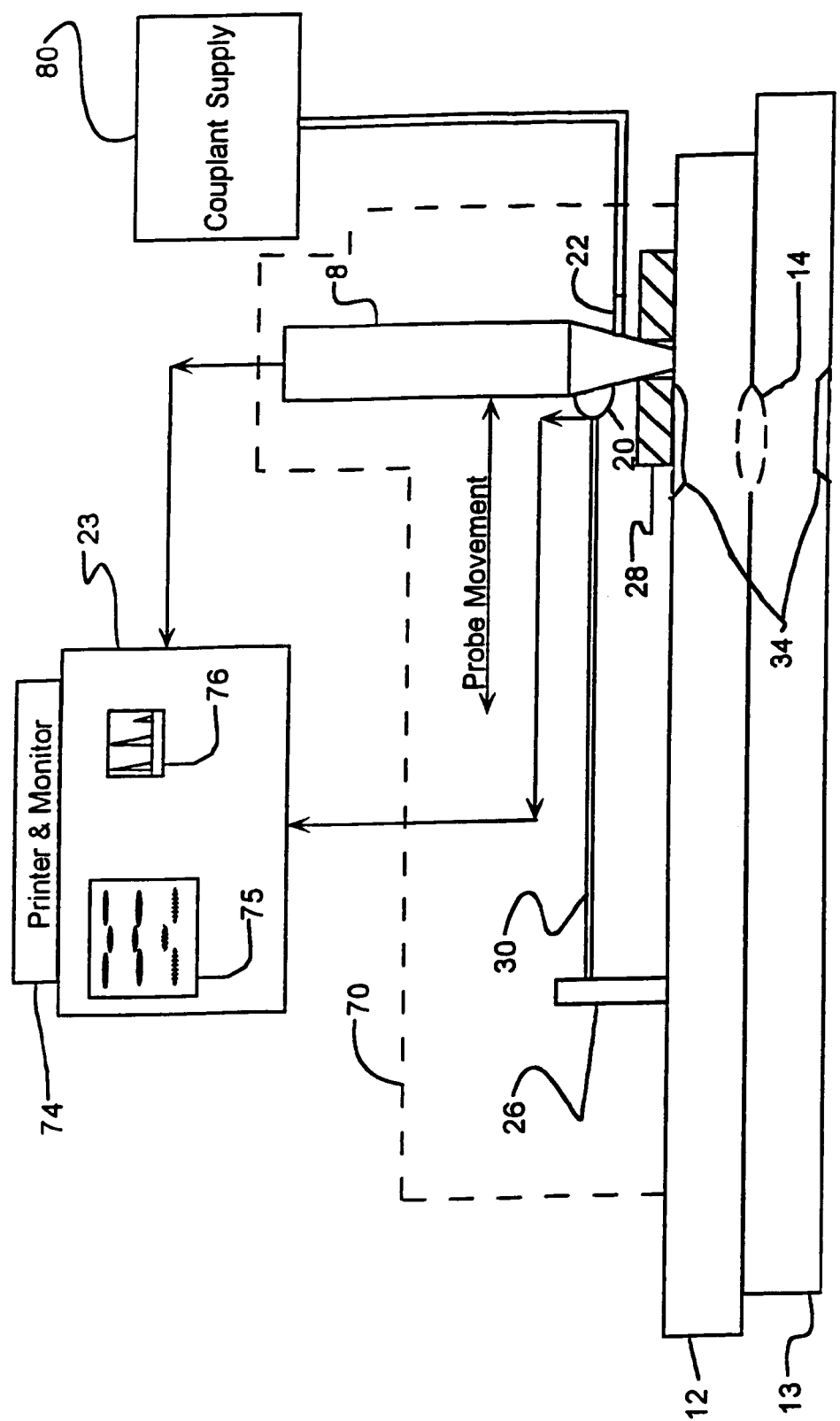
FIG. 8 is a system block diagram of the present invention.

FIG. 8 is a block diagram of the system of the present invention with which inspections to determine the integrity of weldments and to obtain dimensional measurements of the present invention discussed above can be made. What is shown here is the interconnection of the probe 8 of FIG. 3 with the full measurement system including couplant supply 80 with tubing connecting same to couplant inlet 22, data acquisition system 23 with the cables to probe 8 and encoder 20, welder indentations 34 in plates 12 and 13 opposite weldment 14 between plates 12 and 13, and an indication of the direction of travel of probe 8 when it is moved during a scan. Data acquisition system 23 includes a pulser/receiver, a digitizer, a data acquisition unit and a data analysis unit. Attached to data acquisition system 23 is monitor/printer 74. A recording instrument in the form of a printer or magnetic recorder records the A-, B- and C-scan images from the monitor to provide a hard copy of the inspection results. Representative images Of B-scan 75 and A-scan 76 are shown in data acquisition system 23 as they might appear on the monitor. B-scan and C-scan images are difficult to draw and these drawings are an idealized version of actual images.

Figure 9:
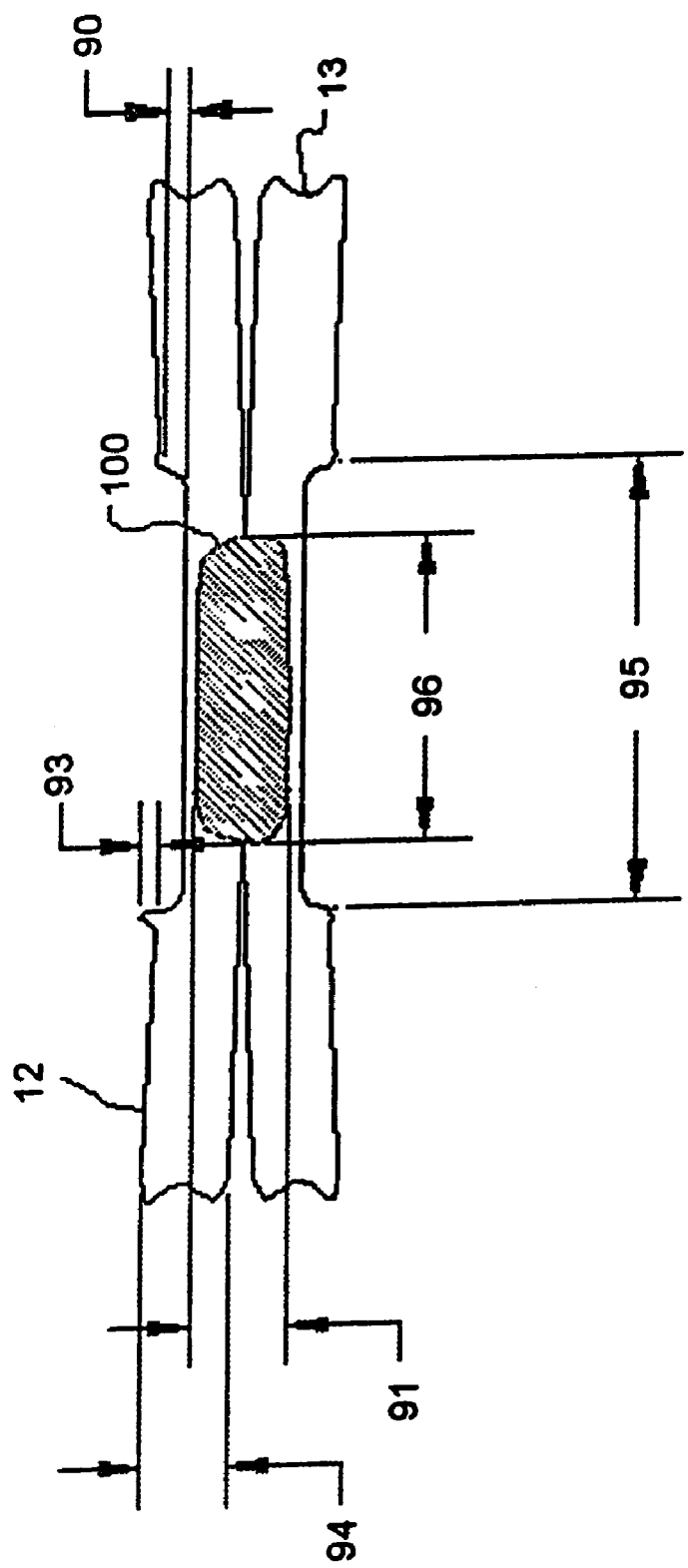
FIG. 9 illustrates a spot weld cross section showing representative dimensions that are practical to be measured using the probe of the present invention.

FIG. 9 is a drawing of a representative cross section of a typical resistance spot weld 100 between plates 12 and 13. The dimensions shown here illustrate the weldment dimensions that can be obtained using the B-scan and C-scan techniques of the present invention. These include the spot weld nugget 96 width and area. Additionally, use of the special probe 8 and scanner 70 arrangement as described in relation to, and shown in, FIG. 3, additional measurements can be made that include: indentation depth 90 and width 95, top plate 12 thickness (t) 94, plate distortion 93, and welded thickness ($t_w$) 91.

Figure 10:
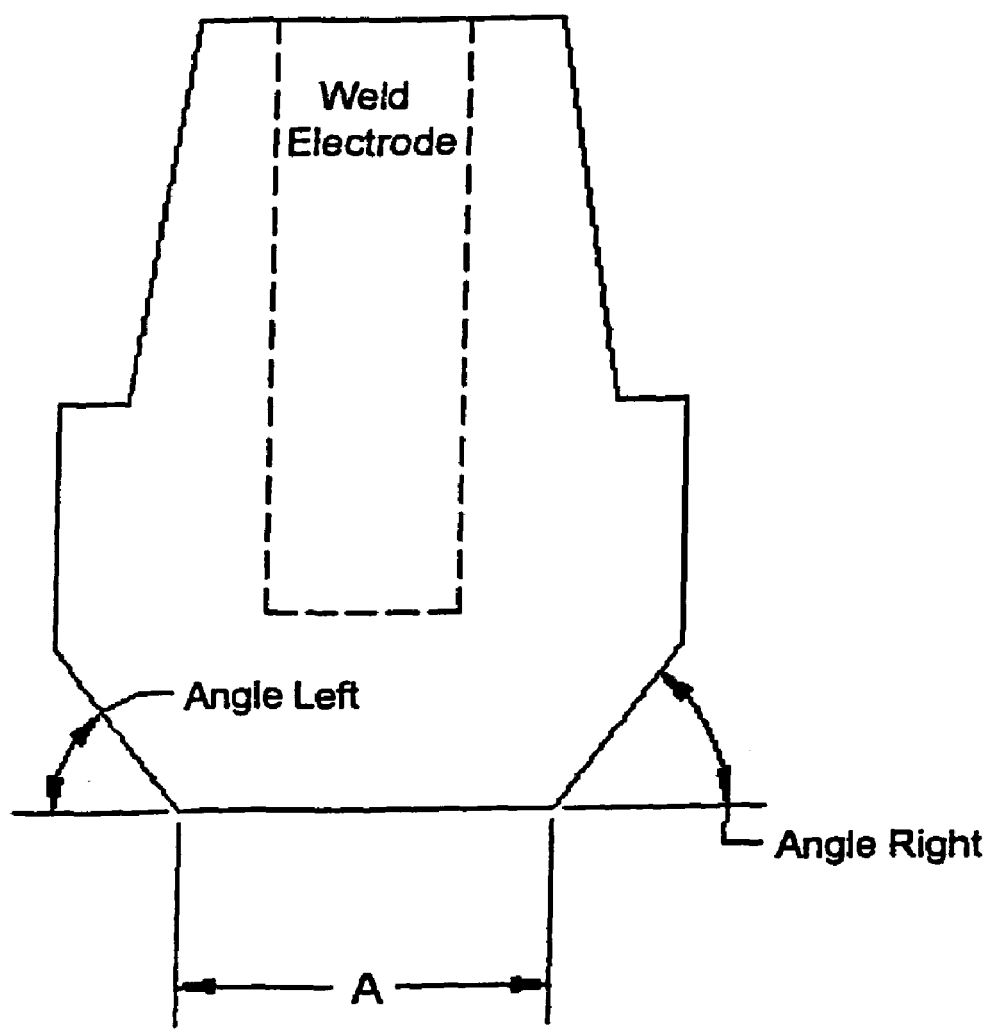
FIG. 10 illustrates the nominal size and shape of a typical weld electrode.

FIG. 10 has been included to illustrate the nominal size, shape and proportions of a typical weld electrode for use with sheet steel, however, there are other shapes of electrodes in common use. The portions of the electrode that create the surface impression on the material being internally weld is the size and shape of the face together with the bevel angle adjacent the face. Typically the face of an electrode is round with a diameter A and the bevel angle is typically 45°±1°. The dimensions and shape of the nose of the electrode substantially determine the shape of the weld impression. The depth of the weld impression is substantially determined by three other factors: the material type, the pressure applied to the material by the face of the electrode during welding, and the amount of heat generated during the welding process. The other dimensions and shape of the electrode shown in FIG. 10 are more generally dictated by the welding machine tooling and for heat distribution in the electrode and have little or no effect on the size, shape and depth of the weld impression. Sample dimensions of a weld electrode of FIG. 10 are given in FIG. 11.

The list below provides representative calculations that are enabled by the present invention. These calculations are typically made with a computer from the various measures of the spot weld characteristics and have been included here to illustrate that these calculations are practical using the methods and apparatus of the present invention.

10-1. Plate thickness (tm)=ultrasonic velocity in plate material* ($t_n - t_{n-1}$)

Calculated in region near start or end of scan. Where $t_n$ is the time of flight for the ultrasonic signal return from surface "n" following the previous ultrasonic signal in this region. Usage is as input to a table of acceptable weld diameters to be used in production.

10-2. Criteria for button diameter=4*SQRT(tm)

10-3. Spot Welding Electrode Impression Dimension (requires curve fit of B-scan and C-scan data) (see FIG. A1—The Dimension 1 and Angle$_{left}$ and Angle$_{right}$ of Specification for Resistance Welding of Carbon and Low-Alloy Steels, American Welding Society, AWS C1.4M/C1,4:1999)

10-4. Indentation=ultrasonic velocity of the couplant*(the longest time of flight to the first surface–the time of flight from the first surface (near the edge of the scan)).

10-5. Distortion=ultrasonic velocity of the couplant*(the shortest time of flight to the first surface+the time of flight from the first surface (near the edge of the scan)).

10-6. Yield=number of acceptable welds in weld group=Number of welds acceptable/Number of welds inspected in the group.

10-7. Comparison to Metalagraphic Test.

The SWEPS probe of the present invention can be used with commercial ultrasonic systems to detect cracks, holes, porosity, non-metallic inclusions, and indentation.

The plate thickness can be calculated at the beginning and end of a scan using the equation of 10-1. The plate thickness of 10-1 is then used to calculate, or from a look-up table, to obtain the button dimension(s) with calculation 10-2. The shape of the welding electrode impression 34 (FIG. 8) is determined with a curve fitting algorithm (10-3) to fit the nominal curve for the face of the welding electrode used to the B-scan top surface profile and to the C-scan. The indentation depth calculation 10-4 uses the couplant velocity and the time differences measured for the front surface of plate 12 and the maximum distance to the electrode impression fit from 10-3. Distortion calculation 10-5 uses the areas of the scan to compute a reference plane through representative points from the image, then locates and removes the weld tool impression so that variations from the plane can be calculated ignoring the tool impression. Yield calculations 10-6 report the number of welds tested, passed, and the types of failures, and flag changes in the statistics of the measurements. Weld defects can also be detected using various classification criteria to identify the presence of each type to manufacturing (e.g., excessive inclusions in plate 12 causing bad welds). Item 10-7 is included to indicate that the probe of the present invention can be used with presently available ultrasonic test equipment to detect weldment cracks, holes, porosity, non-metallic inclusions, and indentations.

As discussed above the methods and apparatus of the present invention present may advantages and is capable of making calculations not heretofore possible. In the above discussion an embodiment of the invention has been provided together with several examples of calculations that are possible with the present invention and suggested formulas for making those calculations. One skilled in the art will recognize that the same results provided by the present invention could be achieved with different or modified formulas. It is to be understood that the present invention is not limited to only that discussed above, and that it also includes equivalents of those disclosed. Therefore the present invention is only to be limited by the scope of the claims.

What is claimed is:

1. A non-destructive, non-immersion, open air method for ultrasonically measuring a weldment between materials, the method comprises the steps of:
   a. selecting an ultrasonic signal sending and receiving probe with an ultrasonic transducer and a nose piece sized to be substantially the same size as an electrode indentation corresponding to the weldment to be measured;
   b. placing the nose piece of the ultrasonic signal sending and receiving probe on an external surface of the material;
   c. transporting said probe in a selected path along the external surface of the material with the nose piece sliding on high points of the material to maintain the ultrasonic transducer of the probe a fixed stand-off distance from the external surface of the material as ultrasonic signals are applied to and received from the surface of the material;
   d. determining time between each ultrasonic signal applied to the external surface and each ultrasonic signal received from the external surface;
   e. measuring distance traveled by the probe along the path with the measured distance travel coordinated in time application and receipt of ultrasonic signals to and from the material; and
   f. determining weldment characteristics from the results obtained in steps d. and e.

2. The method as in claim 1 further comprising the step of:
   g. providing and maintaining a couplant between the nose piece and external surface of the material.

3. The method as in claim 1 wherein the nose piece provides a steady reference against the external surface of the material, allowing accurate measurements of the surface, thickness and electrode impression of the material.

4. The method as in claim 1 wherein the nose piece continuously follows the external surface of the material.

5. The method as in claim 1 wherein step f. includes the steps of generating of A, B and C scans of the material.

6. The method as in claim 1 wherein step f. includes the steps of:
   g. determining the thickness of the material;
   h. determining a diameter of the weldment;
   I. determining a dimension of a external surface impression caused by a spot welding electrode when forming the weldment;
   j. determining an indentation depth caused by the spot welding electrode when forming the weldment;
   k. determining the extent of distortion of the external surface of the material caused during forming the weldment;
   l. determining the yield of acceptable weldments from a group of inspected weldments; and
   m. detecting cracks, holes, porosity, non-metallic inclusions and indentation of weldments and at weldment sites.

7. An ultrasonic scanner to open air, non-destructively scan an external surface of a material to generate data to determine characteristics of weldments in the material comprising:
   an ultrasonic transducer to generate and receive ultrasonic signals applied to and received from the external surface of the material;
   a body sized and shaped to hold the ultrasonic transducer and having a nose piece to interface with the external surface of the material to direct signals from the ultrasonic transducer to the surface and to focus ultrasonic signals received from the surface onto the ultrasonic transducer; and
   a distance measurement device in contact with the surface of the material to determine travel distance of the body at any point in time as the body is transported across the surface of the material;
   wherein said nose piece is sized to be substantially the same size as an electrode indentation corresponding to the weldment to be measured with the nose piece sliding on high points of the material to maintain the ultrasonic transducer a fixed stand-off distance from the external surface of the material.

8. The ultrasonic scanner as in claim 7 further comprising a couplet means to provide and maintain a couplant between the nose piece and the surface of the material.

9. The ultrasonic scanner as in claim 7 wherein the nose piece is sized to provide a steady reference against the external surface of the material, allowing accurate measurements of the surface, thickness and electrode impression of the material.

10. The ultrasonic transducer as in claim 7 wherein the nose piece surface is sized and shaped to continuously follow the external surface of the material.

11. A non-destructive, open air measurement system to non-destructively determine characteristics of weldments in a material, without immersion of the material, comprising:
   a scanner including:
      an ultrasonic transducer to generate and receive ultrasonic signals applied to and received from the external surface of the material;
      a body sized and shaped to hold the ultrasonic transducer and having a nose piece to interface with the external surface of the material to direct signals from the ultrasonic transducer to the surface and to focus ultrasonic signals received from the surface onto the ultrasonic transducer; and
      a distance measurement device in contact with the surface of the material to determine travel distance of the body at any point in time as the body is transported across the surface of the material;
      wherein said nose piece is sized to be substantially the same size as an electrode indentation corresponding to the weldment to be measured with the nose piece sliding on high points of the material to maintain the ultrasonic transducer a fixed stand-off distance from the external surface of the material; and
   a processor coupled to the scanner to:
      trigger the scanner to transmit an ultrasonic signal to the surface of the material;
      receive a signal from the scanner for each ultrasonic signal being received from the material;
      receive signals from the scanner corresponding to the position of the scanner at least whenever the scanner is triggered to send signals to the material and when the scanner receives signals from the material; and
      determine characteristics of the weldment from the timing signals and scanner travel distance.

12. The measurement system as in claim 11, the scanner further comprising a couplet means to provide and maintain a couplant between the nose piece and the surface of the material.

13. The measurement system as in claim 11 wherein the nose piece of the scanner acts is sized to provide a steady reference against the external surface of the material, allowing accurate measurements of the surface, thickness and electrode impression of the material.

14. The measurement system as in claim 11 wherein the of the scanner nose piece surface is sized and shaped to follow the external surface of the material.

15. The measurement system as in claim 11 wherein the processor generates of A, B and C scans of the material.

16. The measurement system as in claim 11 wherein the processor determines the thickness of the material, a diameter of the weldment, a dimension of a external surface impression caused by a spot welding electrode when forming the weldment, an indentation depth caused by the spot welding electrode when forming the weldment, the external surface of the material caused during forming the weldment, the yield of acceptable weldments from a group of inspected weldments, and detects cracks, holes, porosity, non-metallic inclusions and indentation of weldments and at weldment sites.

* * * * *